(12) United States Patent
Chiu et al.

(10) Patent No.: US 9,261,504 B1
(45) Date of Patent: Feb. 16, 2016

(54) METHOD AND KIT FOR DETECTION OF HEMOLYTIC UREMIC SYNDROME AND NECROTIZING PNEUMONIA IN CHILDREN WITH PNEUMOCOCCAL DISEASE USING SERUM FETUIN-A LEVELS AS A BIOMARKER

(71) Applicants: Cheng-Hsun Chiu, Taoyuan County (TW); Rajendra Prasad Janapatla, Taoyuan County (TW); Chyi-Liang Chen, Taoyuan County (TW)

(72) Inventors: Cheng-Hsun Chiu, Taoyuan County (TW); Rajendra Prasad Janapatla, Taoyuan County (TW); Chyi-Liang Chen, Taoyuan County (TW)

(73) Assignee: Chang Gung Medical Foundation, Taipei (TW)

( * ) Notice: Subject to any disclaimer, the term of this patent is extended or adjusted under 35 U.S.C. 154(b) by 0 days.

(21) Appl. No.: 14/497,989

(22) Filed: Sep. 26, 2014

(51) Int. Cl.
*G01N 33/58* (2006.01)
*G01N 33/60* (2006.01)
*G01N 33/68* (2006.01)
*G01N 33/569* (2006.01)

(52) U.S. Cl.
CPC .... *G01N 33/56938* (2013.01); *G01N 33/56944* (2013.01); *G01N 33/68* (2013.01); *G01N 33/581* (2013.01); *G01N 33/582* (2013.01); *G01N 33/60* (2013.01); *G01N 2469/10* (2013.01)

(58) Field of Classification Search
None
See application file for complete search history.

(56) References Cited

PUBLICATIONS

Takaishi M. Nihon Kyobu Shikkan Gakkai zasshi 28: 315-319, 1990, abstract.*

* cited by examiner

*Primary Examiner* — S. Devi

(57) ABSTRACT

The invention provides a method and a kit for measuring the levels of serum fetuin-A in children to reflect the severity of invasive pneumococcal diseases caused by *Streptococcus pneumoniae*, including necrotizing pneumonia and hemolytic uremic syndrome. The mean fetuin-A levels in the HUS patients are significantly lower (207±80 mg/L, p<0.001) when compared to patients with lobar pneumonia (610±190 mg/L) and the healthy controls (630±250 mg/L). A serum fetuin-A level is a useful biomarker to classify the severity of pneumococcal infection in children. The level of biomarker fetuin-A can be monitored and evaluated by enzyme linked immunosorbent assay and Western blot hybridization.

3 Claims, 9 Drawing Sheets

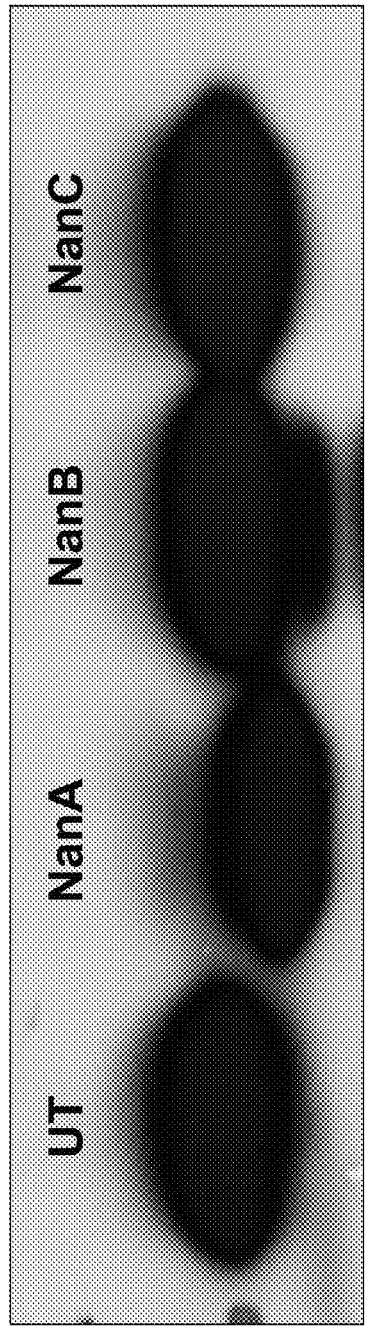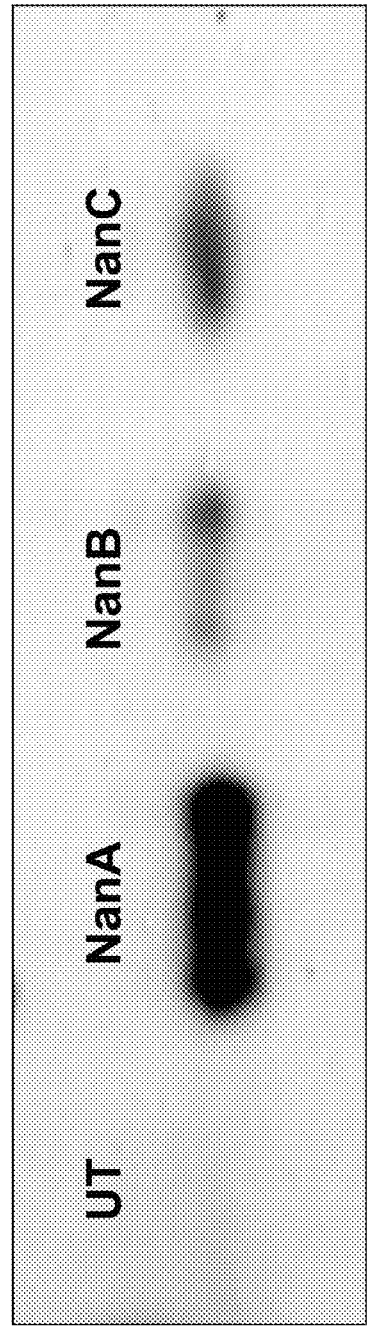
FIG. 3A
FIG. 3B

METHOD AND KIT FOR DETECTION OF HEMOLYTIC UREMIC SYNDROME AND NECROTIZING PNEUMONIA IN CHILDREN WITH PNEUMOCOCCAL DISEASE USING SERUM FETUIN-A LEVELS AS A BIOMARKER

FIELD OF THE INVENTION

The invention provides a method and kit for detecting severe invasive pneumococcal diseases caused by *Streptococcus pneumoniae*, including necrotizing pneumonia and hemolytic uremic syndrome, based on the levels of serum fetuin-A in children. A serum fetuin-A level is a useful biomarker to classify the severity of pneumococcal infection in children. The level of biomarker fetuin-A can be robustly monitored and evaluated by enzyme-linked immunosorbent assay and Western blot hybridization.

BACKGROUND OF THE INVENTION

*Streptococcus pneumoniae* can colonize the upper respiratory tract of humans and subsequently cause mucosal infections such as sinusitis, otitis media, and pneumonia, and also invasive pneumococcal diseases (IPD) including complicated pneumonia (empyema and necrotizing pneumonia), bacteremia, and meningitis. One of the most severe complications of IPD is hemolytic uremic syndrome (HUS), which mainly occurs in children and is associated with hemolytic anemia, thrombocytopenia and acute renal failure (HUS triad). In HUS patients, pneumococcal neuraminidase cleaves N-acetylneuraminic acid (sialic acid) residues on red blood cells (RBC) leading to the exposure of the Thomsen-Friedenrich antigen (T-antigen; TA) on cells and allowing normally circulating anti-TA antibodies to react with the exposed TA to form immune complex and subsequent lysis of the cells. In a recent study, we examined the distribution of three neuraminidase genes (nanA, nanB and nanC) in pneumococcal isolates derived from HUS patients and those without. *S. pneumoniae* intrinsically carried nanA and nanB, while relative to 89% of the HUS isolates that harbored nanC, only 42% of the IPD isolates from the controls carried the gene. We thus speculated that NanC might contribute to the risk of developing HUS in an additive manner in the presence of NanA and NanB by increasing the overall activity of pneumococcal neuraminidases, and so was associated with the occurrence of HUS following pneumococcal infection.

Neuraminidase-producing organisms, like *S. pneumoniae*, acquire sialic acid by cleaving host sialo-glycoconjugates and use it as their carbon and nitrogen source. During pneumococcal infection, cleavage of sialyl linkages to expose TA in host cells might be due to a higher neuraminidase activity from NanA, NanB, or NanC or an additive effect of the three. Previously, *S. pneumoniae* serotype 2 (strain R6) and serotype 4 (strain TIGR4) were used to confirm α2-3 sialyl linkages specificity of the NanB and NanC produced. Recently, a report showed that NanA and NanB mutants of *S. pneumoniae* are deficient in adherence to three epithelial cell lines, as well as to primary nasopharyngeal cells. In the respiratory tract, distribution of α2-3 and α2-6 sialyl linkages varies depending on age, tissue and cell types; α2-3 linkages are selectively present on goblet cells and secreted mucins and α2-6 linkages on ciliated respiratory epithelial cells. Additional presence of NanC in *S. pneumoniae* may therefore help the pathogen to acquire more sialic acid from the respiratory tract during colonization and infection.

Detection of TA activation using peanut agglutinin (PNA) was thought to be the most appropriate test to support the diagnosis of pneumococcal HUS. Pneumococcal HUS is a well-characterized condition but continues to be under recognized. To improve the under-diagnosis and late detection of HUS, more specific laboratory tests are needed. This study adds fetuin-A as a biomarker to predict severe IPD, such as HUS and complicated pneumonia.

SUMMARY OF THE INVENTION

Serum sialoglycoproteins are rich sources of sialic acids. Through the analysis of a profile of serum sialoglycoproteins after neuraminidase treatment using state of the art proteomic instrument, we identified an abundant sialoglycoprotein fetuin-A (also known as the α2-Heremans-Schmid glycoprotein AHSG) that is the target of neuraminidase activity in severe pneumococcal infection, and results in significantly declining the level of serum fetuin-A. To determine the level of fetuin-A in the sample, the techniques comprising enzyme linked immunosorbent assay, Western blot hybridization, immunofluorescence labeling, radioimmunoassay, immunoradiometric assay, and combination thereof can be utilized.

Since neuraminidases could selectively release all the sialic acid residues with different linkages, we investigated that serum fetuin-A steady state levels may change during infection, and hence the role of serum fetuin-A level can be a biomarker to predict severe pneumococcal infections.

By both qualitative and quantitative analyses of serum fetuin-A and other sialoglycoproteins in pneumococcal infections, complicated pneumonia with HUS caused by *S. pneumoniae* and differentiate IPD from other infections may be confirmed. Serial level of fetuin-A is also of potential to reflect children patients' response to therapy and recovery from HUS. Fetuin-A is a useful biomarker for severe IPD.

BRIEF DESCRIPTION OF THE DRAWINGS

FIG. 3A: NanA, NanB and NanC differentially cleave serum sialoglycoproteins. Western blot to detect fetuin-A with anti-fetuin A antibody in total serum after NanA, NanB and NanC treatment as well as the untreated control without neuraminidase treatment (UT) are shown.

FIG. 3B: NanA, NanB and NanC differentially cleave serum sialoglycoproteins. Western blot to detect asialo-fetuin captured from total serum by peanut lectin after NanA, NanB and NanC treatment as well as the untreated control without neuraminidase treatment (UT) are shown.

DETAILED DESCRIPTION OF THE INVENTION

NanC Showed Substrate Specificity of α2-3 Linkages

Figure 1A:
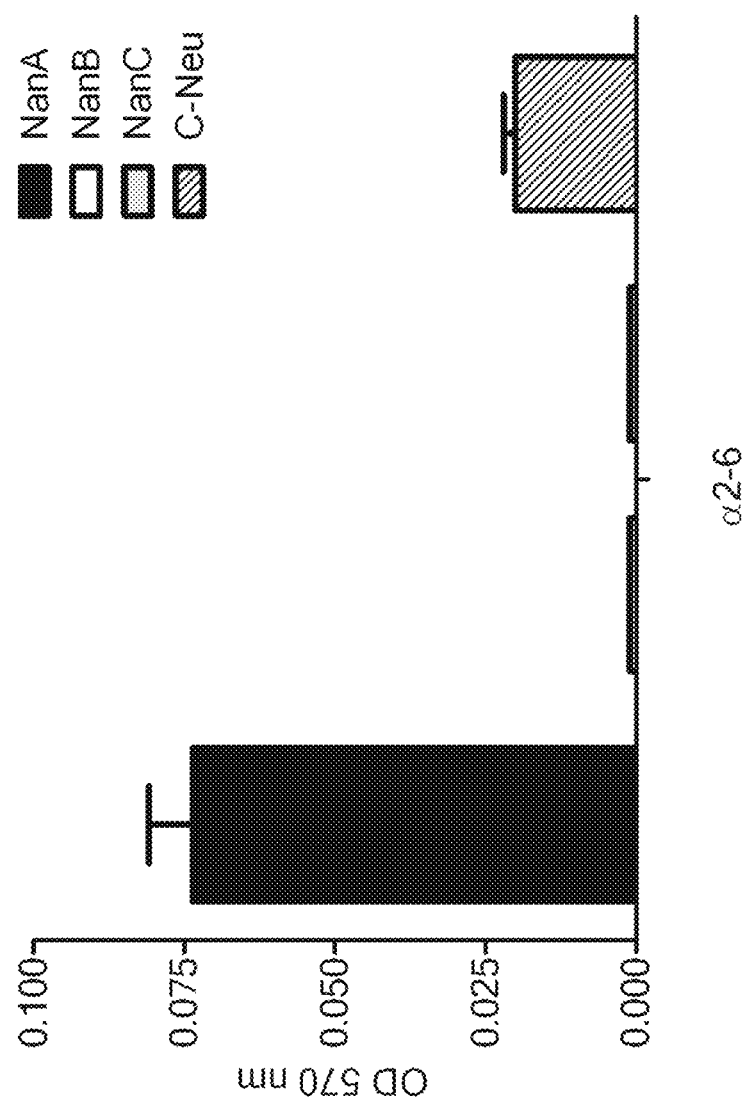
FIG. 1A: Substrate specificity of NanA, NanB and NanC. α2-6 sialyllactose was used to analyze α2-6 sialic acid link specificity. C-Neu is *Clostridium perfringens* neuraminidase that was used as a control.
Figure 1B:
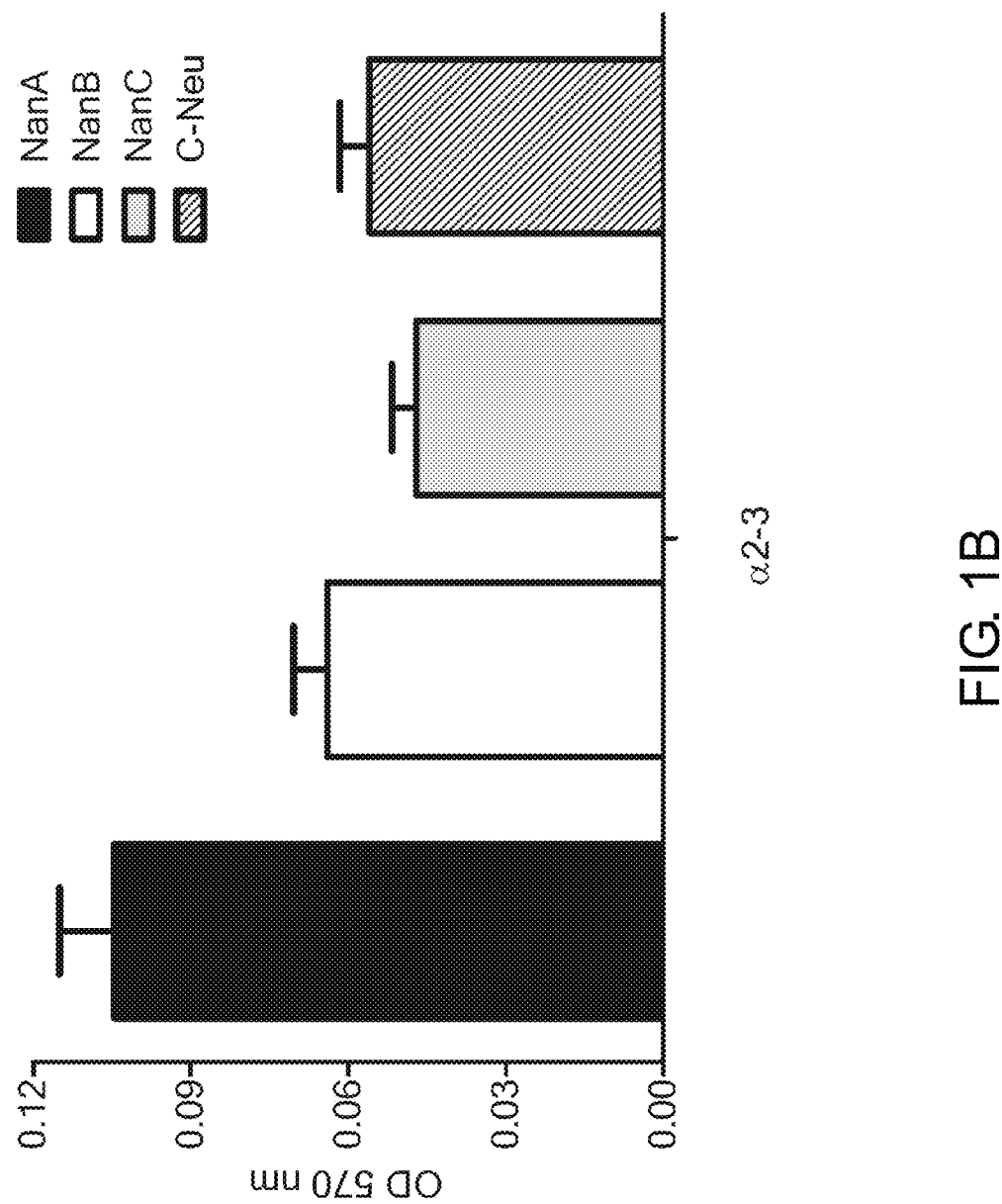
FIG. 1B: Substrate specificity of NanA, NanB and NanC. α2-3 sialyllactose was used to analyze α2-3 sialic acid link specificity. C-Neu is *Clostridium perfringens* neuraminidase that was used as a control.
Figure 2A:
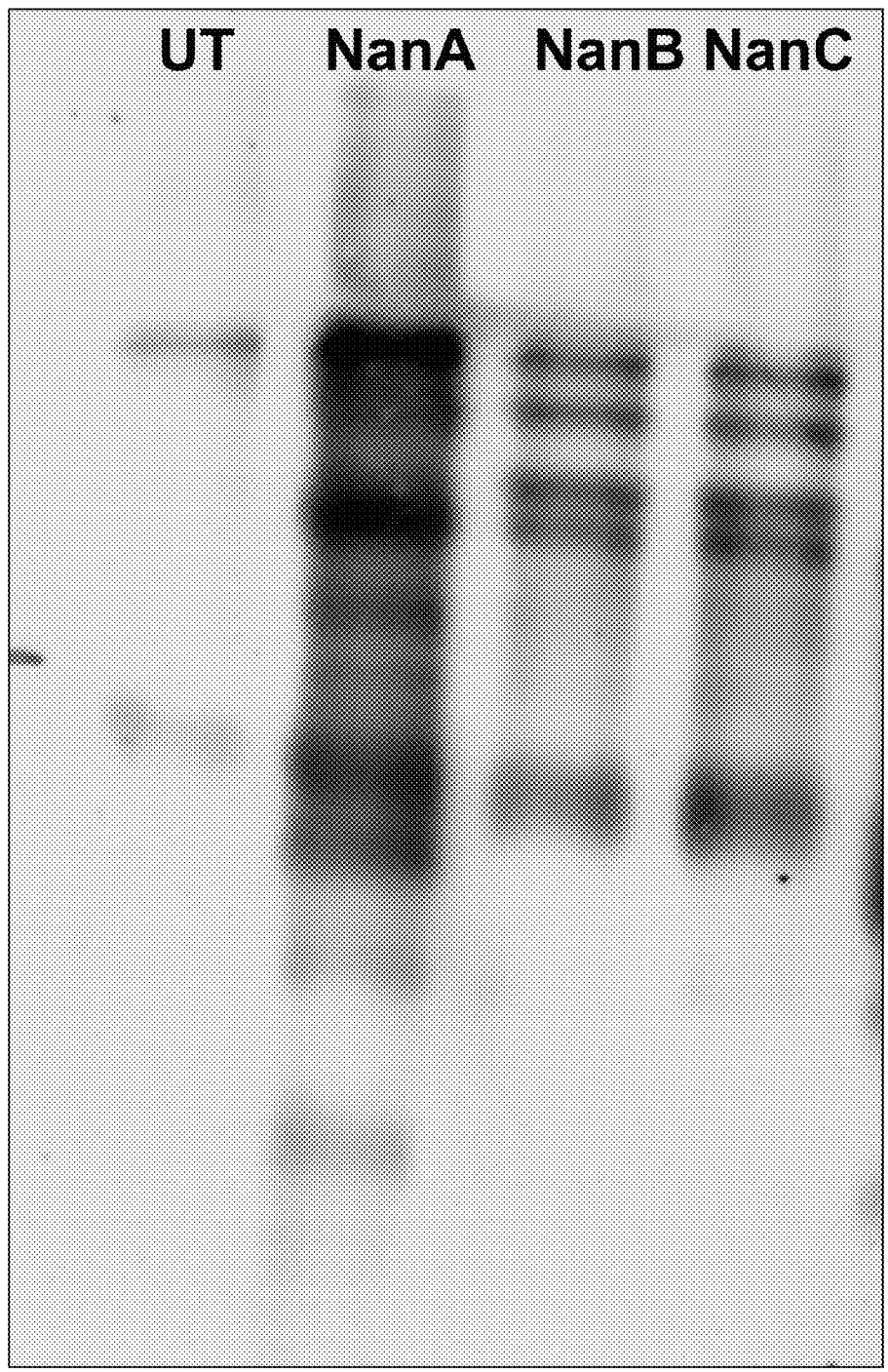
FIG. 2A: NanA, NanB and NanC differentially cleave serum sialoglycoproteins. Western blot of biotinylation-pretreated asialoglycoproteins after NanA, NanB and NanC treatment as well as the untreated control without neuraminidase treatment (UT) and captured by peanut lectin column is shown using streptavidin-HRP for the detection of the biotinylated proteins.
Figure 2B:
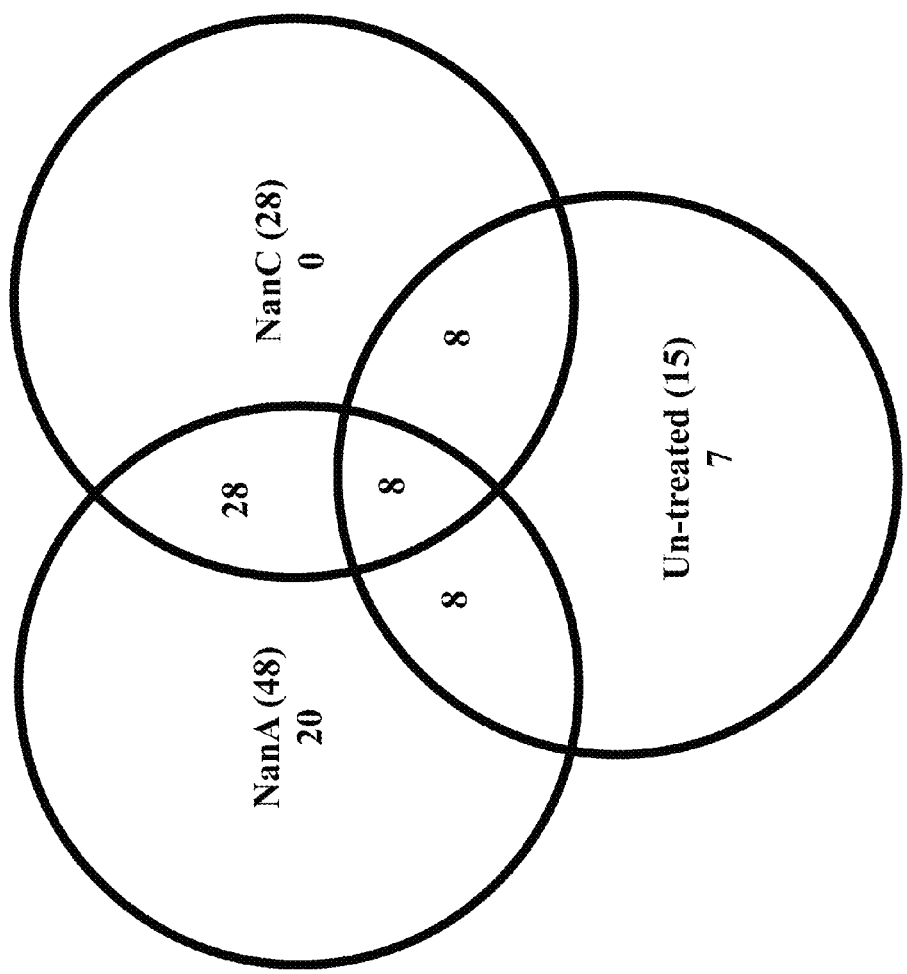
FIG. 2B: Venn diagram of number of T antigen-containing glycoproteins identified in untreated and neuraminidase-treated serum by LC-MS/MS. Numbers in parentheses 15, 48, and 28 indicate proteins detected in the untreated (UT), NanA- and NanC-treated, respectively. Numbers 7, 20 and 0 indicate proteins unique to untreated (UT), NanA- and NanC-treated, respectively. Venn diagram also shows the overlaps of proteins detected. Eight proteins (in intersection) were found to be common in both untreated and treated neuraminidase samples.
Figure 4:
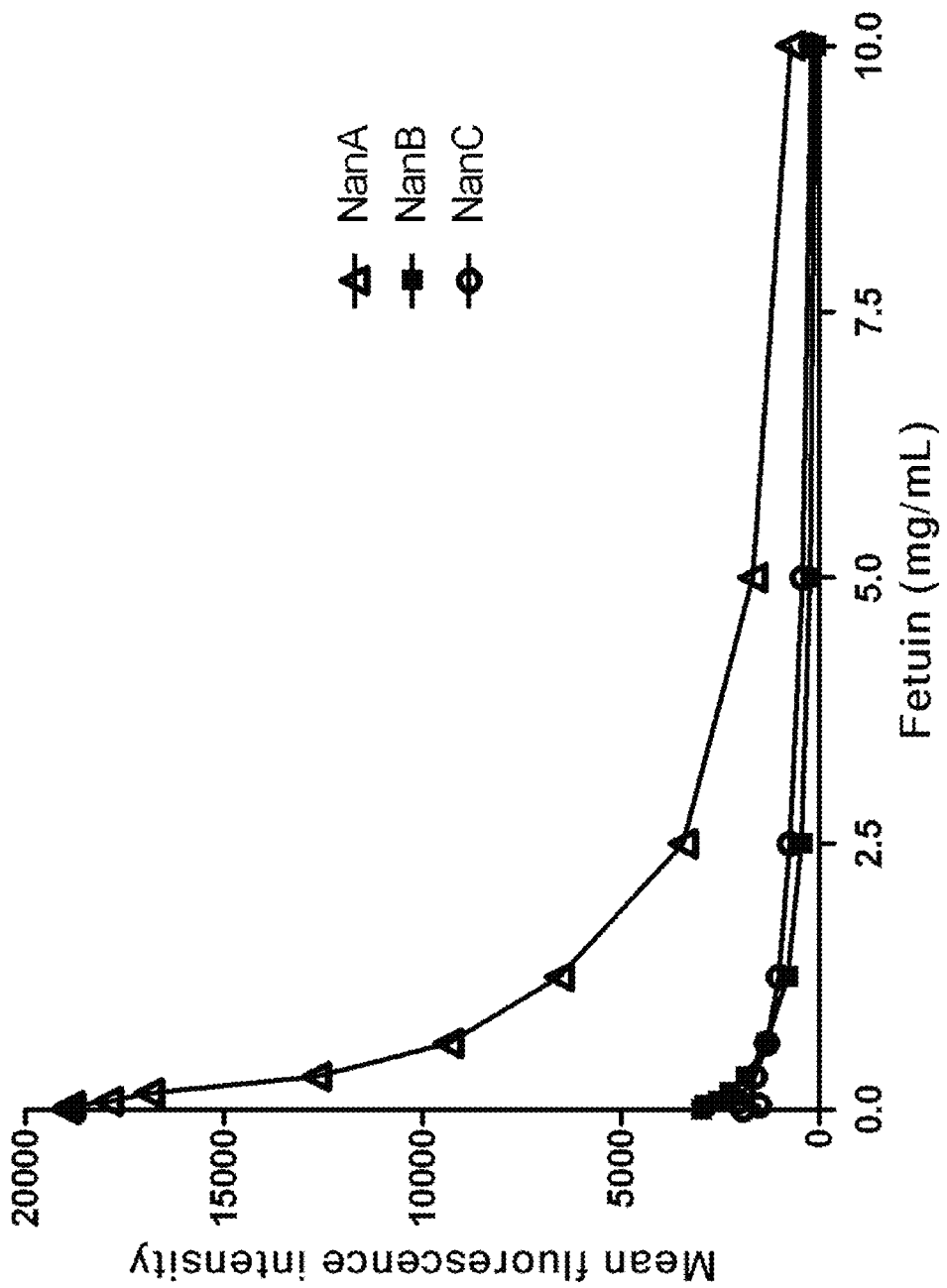
FIG. 4: Fetuin-A inhibits neuraminidase-mediated T antigen (TA) exposure on RBC. Neuraminidases used include NanA, NanB and NanC. MFI represents the mean fluorescence intensity values. Fluorescein labeled Peanut Agglutinin (fluorescein-PNA) was used to detect TA on red blood cells (RBC).
Figure 5:
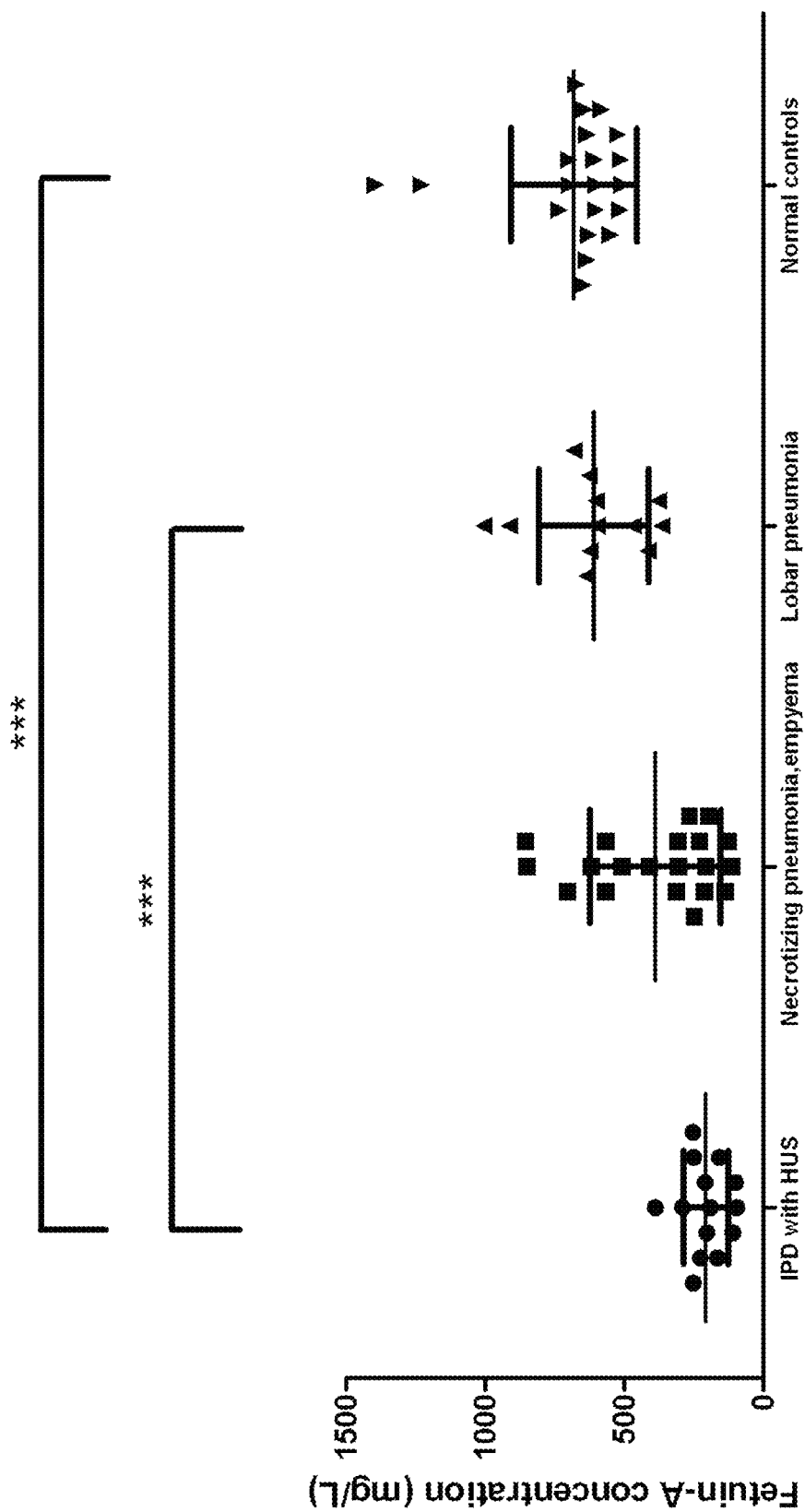
FIG. 5: Fetuin-A levels of sera in patients with HUS, empyema of necrotizing pneumonia, and lobar pneumonia, and those in normal persons. *** indicates P<0.001.

In this study, NanA only showed cleavage activity against α2-6-linked sialyllactose (FIG. 1A), and higher activity against α2-3-linked sialyllactose, compared to NanB and NanC (FIG. 1B). However, NanC, similar to NanB, exhibited cleavage activity against α2-3-linked sialyllactose while both showed no activity against α2-6 (FIG. 1A and 1B). C-Neu purchased from Sigma® is *Clostridium perfringens* neuraminidase that was used as a positive control.
NanA, NanB and NanC Cleaved Fetuin-A and Other Sialoglycoproteins in Human Serum Peanut agglutinin (PNA) binds preferentially to a commonly occurring structure, galactosyl (β-1,3)N-acetylgalactosamine (TA). To identify serum sialoglycoproteins that are targeted by pneumococcal neuraminidases, asialoglycoproteins were captured by peanut lectin conjugated agarose column, eluted by 200 mM lactose, and analyzed by Western blot hybridization. After the sera were treated with neuramindases and biotinylated, we carried out PNA conjugated agarose precipitation with biotinylated sera, followed by Western blot analysis using streptavidin-HRP to detect the biotinylated proteins. Binding specificity of TA exposed glycoproteins with PNA was confirmed by using lactose in control precipitations. As shown in FIG. 2A, when the blot was probed with streptavidin-HRP, multiple proteins were detected in the NanA-, NanB- and NanC-treated samples. However NanB- and NanC-treated samples showed a similar protein pattern, indicating similar sialoglycoproteins specificity. LC/MS analysis for proteins eluted from the PNA agarose column resulted in identification of 15, 48, and 28 proteins in the untreated, NanA- and NanC-treated samples, respectively. Immunoglobulins, apolipoproteins, fibrinogens, keratins, and complement system proteins were predominantly desialylated by NanA and NanC. Venn diagram shows the overlap of proteins detected by LC-MS/MS (FIG. 2B). Eight proteins were found to be common in both untreated and neuraminidase-treated samples. All the 28 proteins identified in NanC-treated samples were also identified in NanA-treated samples; all the remaining 20 proteins were unique to NanA. The results suggest a broader cleavage activity of NanA on serum sialoglycoproteins. Fetuin A glycoprotein was positively identified in the peptide sequence information obtained from LC/MS. We further confirmed the presence of fetuin-A in the eluent from the PNA-agarose precipitation by Western blotting. As shown in FIGS. 3A and 3B, Western blot analysis of samples using an anti-Fetuin-A antibody (Santa Cruz Biotechnology, Inc., USA) revealed a band of about 55 kDa in each of NanA-, NanB- and NanC-treated sera in the cases with and without PNA-agarose precipitation. However, this band was absent in the untreated sera in the case of PNA-agarose precipitation, indicating that fetuin-A without the treatments of NanA, NanB, and NanC could not be captured by PNA-agarose. Western blot analysis also revealed a higher intensity band in NanA-treated sera when compared to NanB- and NanC-treated sera. This might be due to the broader activity of NanA on both α2-6 and α2-3 sialyl linkages on fetuin-A. This may also reflect the multiplicity in the Galβ1-3GalNAcα content on fetuin-A and other asialoglyoproteins, such that proteins containing more residues of this sugar are selectively precipitated (FIG. 2B). Presence of fetuin-A in neuraminidases-treated and the untreated sera were confirmed by Western blot hybridization with an anti-fetuin-A antibody. NanA-treated samples showed a lower fetuin-A band likely due to desialylation of both α2-6 and α2-3 sialyl linkages when compared to the untreated samples (FIG. 3A).
Bovine Fetuin Competitively Inhibited Pneumococcal Neuraminidases Neuramindase activity of NanA was higher than NanB and NanC when bovine fetuin (Sigma, Saint Louis, Mo., USA) was used as a substrate Inhibition of TA exposure on RBC cells ($3 \times 10^7$ cells/mL) carried out by NanA, NanB and NanC was quantitatively analyzed by fluorescein-PNA (Vector Laboratories, Burlingame, Calif., USA) in the presence of bovine fetuin (0~10 mg/mL) for one hour at 37° C. Labeling was done at 4° C. with PNA and flow cytometric analysis (FACScan, Becton Dickinson, USA) was performed using 10,000-20,000 RBC cells. NanA, NanB and NanC activity was inhibited by bovine fetuin in a dose-dependent manner; 50% inhibition to each of 1 μg NanA, NanB and NanC was observed in the presence of fetuin at 2.59 mg/mL, 2 mg/mL and 1.2 mg/mL, respectively (FIG. 4).
Fetuin-A Levels as A Biomarker to Predict HUS and Complicated Pneumonia in Patients with IPD Enzyme-linked immunosorbent assay (ELISA) with a sandwich ELISA kit (detectable range, 0.16 to 1.74 ng/ml, Human fetuin-A ELISA kit, R&D Systems, Minneapolis, Minn., USA) was used for the measurement of human serum fetuin-A. We found that the mean fetuin-A level in the HUS patients was significantly lower (207±80 mg/L, p<0.001) when compared to patients with lobar pneumonia (610±190 mg/L) and the healthy controls (630±250 mg/L) (FIG. 5). Although the mean fetuin-A level in the patients with necrotizing pneumonia and empyema was lower (390±220 mg/L), the difference was not significant when compared to patients with lobar pneumonia (p<0.73). From a 5-year-old patient with pneumococcal meningitis and brain abscess, three consecutive blood samples were collected to determine the serum fetuin-A concentration. We found that fetuin-A level during acute stage of infection was 236 mg/L only, four weeks later it increased to 609 mg/L and six weeks later to 742 mg/L. This indicates that response to therapy and recovery from IPD could be monitored by measuring serum fetuin-A. The mean age in the tested patients with HUS was 4.05±4.8 years old, which is close to 5.3±0.6 years old in normal controls. *S. pneumoniae* urine antigen test was positive in 93% of HUS patients, 80% in complicated pneumonia and 42% in lobar pneumonia. Sixty-four percent (64%) and 55% of HUS and complicated pneumonia patients respectively, were *S. pneumoniae* culture positive (blood, CSF, or pleural fluid). Lobar pneumonia patients were all *S. pneumoniae* culture negative.

Figure 6A:
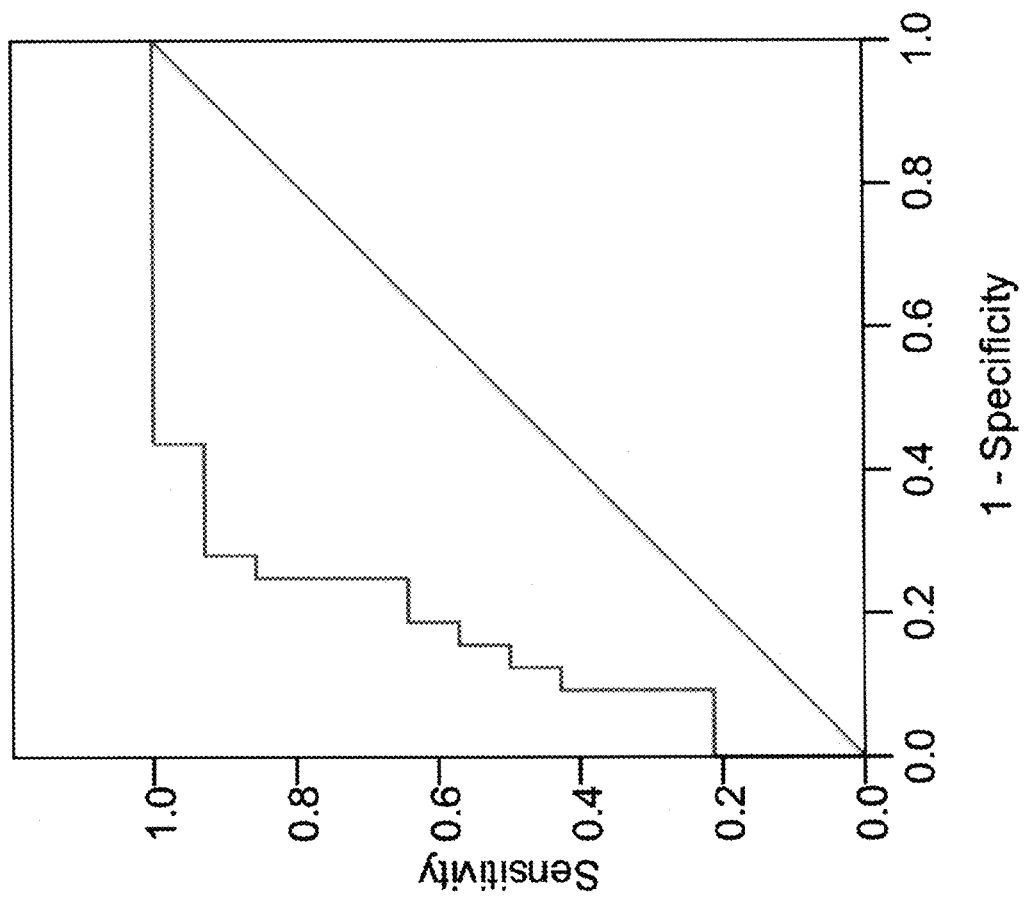
FIG. 6A: ROC curves for fetuin-A levels. Both HUS with necrotizing and lobar pneumonia were compared. The AUC was 0.842; cutoff value 298 mg/L, sensitivity 92.9% and specificity 71.9%.
Figure 6B:
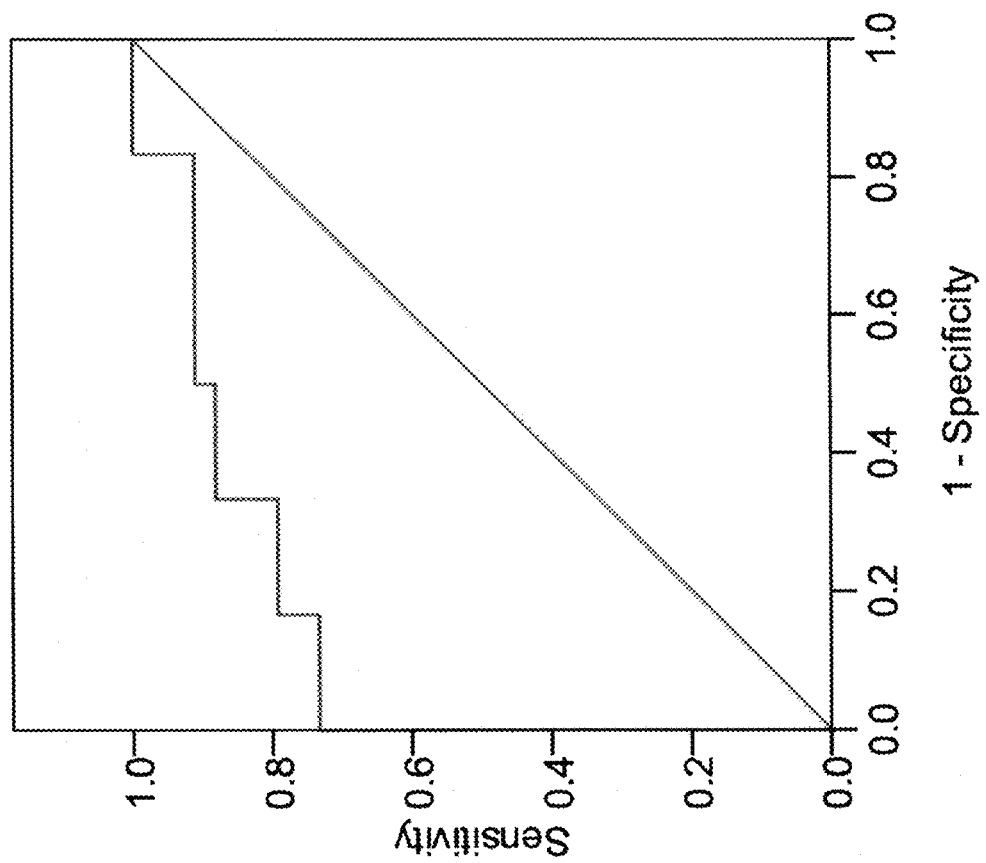
FIG. 6B: ROC curves for fetuin-A levels. Comparing HUS and necrotizing pneumonia with lobar pneumonia the AUC of 0.873, cutoff value 340 mg/L, sensitivity 73.5% and specificity 100%.

Receiver operating characteristic (ROC) curves for fetuin-A level was constructed by comparing patients with HUS and those with complicated pneumonia and lobar pneumonia (CP/LP), as well as patients with HUS and complicated pneumonia and those with lobar pneumonia (FIG. 6A-6B). These curves were used to identify various cutoff values with differing sensitivities and specificities. In comparing HUS with CP/LP, the ROC area under the curve (AUC) was 0.842; a cutoff value of 298 mg/L yielded sensitivity of 92.9% (95% CI: 68.5%-98.7%), specificity of 71.9% (95% CI: 54.6%-84.4%), NPV of 95.8% (95% CI: 79.8%-99.2%), and negative likelihood ratio of 0.36 (95% CI: 0.04-0.36). With a cutoff value of 298 mg/L, five HUS patients with negative *S. pneumoniae* culture and one HUS patient with negative urine antigen test would have been classified as positive for pneumococcus (FIG. 6A). In discriminating HUS and complicated pneumonia from those with lobar pneumonia, the ROC curve had an AUC of 0.873. For this analysis, a cutoff value of 340 mg/L gave a sensitivity of 73.5% (95% CI: 56.9%-85.4%), specificity of 100% (95% CI: 75.8%-100%), NPV of 57.1% (95% CI:36.5%-75.5%), and negative likelihood ratio of 0.27 (95% CI: 0.10-0.68) (FIG. 6B). The results suggest that physicians should watchfully observe patients with IPD for the possibility of developing HUS when their serum fetuin-A level dropped below 298 mg/L, and that a level less than 340 mg/L would be an indicator for complicated pneumonia with or without HUS in patients with suspected pneumococcal infection.

The invention claimed is:

1. A method of detecting an invasive pneumococcal infection with the associated complication of hemolytic uremic syndrome (HUS) or necrotizing pneumonia in a pediatric patient having the infection, the method comprising:
   (a) collecting a serum sample from the pediatric patient having the invasive pneumococcal infection;
   (b) determining the level of sialoglycoprotein fetuin-A in the serum sample, and
   (c) comparing the serum fetuin-A level present in healthy pediatric persons with the fetuin-A level in the serum sample of the pediatric patient having the invasive pneumococcal infection with the associated complication of HUS or the necrotizing pneumonia,
   wherein the mean serum fetuin-A level in the healthy pediatric persons is 630±250 mg/L,
   wherein the mean serum fetuin-A level of 207±80 mg/L in the pediatric patient is indicative that the patient has the invasive pneumococcal infection with the associated HUS and
   wherein the mean serum fetuin-A level of 390±220 mg/L in the pediatric patient is indicative that the patient has the invasive pneumococcal infection with the associated necrotizing pneumonia.

2. The method of claim 1, wherein the determining step uses ELISA, Western blot, immunofluorescence labeling assay, immuno-radioassay, or a combination thereof.

3. The method of claim 1, wherein the method is used to evaluate the response in the pediatric patients to treatment of the invasive pneumococcal infection and recovery therefrom.

* * * * *